United States Patent
Nicolaou et al.

(10) Patent No.: US 8,603,761 B2
(45) Date of Patent: *Dec. 10, 2013

(54) GLP-1 RECEPTOR AGONIST BIOASSAY

(71) Applicant: Amylin Pharmaceuticals, LLC, San Diego, CA (US)

(72) Inventors: Michalis Nicolaou, San Diego, CA (US); Frederick Charles Bancroft, Cardiff, CA (US); John Patrick Herich, Cardiff, CA (US); Aung Naing Lwin, Carlsbad, CA (US); Swati Gupta, San Diego, CA (US)

(73) Assignees: Amylin Pharmaceuticals, LLC, San Diego, CA (US); AstraZeneca Pharmaceuticals LP, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/691,421

(22) Filed: Nov. 30, 2012

(65) Prior Publication Data

US 2013/0089878 A1  Apr. 11, 2013

Related U.S. Application Data

(63) Continuation of application No. 12/990,693, filed as application No. PCT/US2009/044135 on May 15, 2009, now Pat. No. 8,329,419.

(60) Provisional application No. 61/055,842, filed on May 23, 2008.

(51) Int. Cl.
  *G01N 33/53* (2006.01)
  *G01N 33/567* (2006.01)

(52) U.S. Cl.
  USPC .................. 435/7.2; 435/7.1; 435/7.21

(58) Field of Classification Search
  None
  See application file for complete search history.

(56) References Cited

U.S. PATENT DOCUMENTS

| 5,527,684 | A | 6/1996 | Mabile et al. |
| 7,087,384 | B2 | 8/2006 | Autiero et al. |
| 2004/0092726 | A1 | 5/2004 | Autiero et al. |
| 2006/0275288 | A1 | 12/2006 | Grihalde et al. |

FOREIGN PATENT DOCUMENTS

| EP | 1290448 | 11/2007 |
| WO | WO 01/96877 | 12/2001 |
| WO | WO 2006/005469 | 1/2006 |
| WO | WO2008/005527 | 1/2008 |

OTHER PUBLICATIONS

Cis Bio International, HTFR Package Insert dated Aug. 7, 2007.
Gabriel et al., Assay and Drug Devt Technologies, US 1(2):291-303 (Apr. 1, 2003): High throughput screening technologies for direct cyclic AMP measurement.
Golla et al., J. Biomolecular Screening 7(6):515-525 (Dec. 1, 2002): A Homogenous Enzyme Fragment Complementation Cyclic Amp Screen for GPCR Agonists.
Hargrove et al., Regulatory Peptides 141:113-119 (2007): Biological Activity of AC3174, a peptide analog of Exendin-4.
Korner et al., J. Nuclear Med 48(5):736-737 (2007): GLP-1 Receptor Expression in Human Tumors and Human Normal Tissues: Potential for in vivo Targeting.
Montrose-Rafizadeh et al., J. Biol. Chem. 272(34):21201-21206 (Aug. 22, 1997): High potency Antagonists of the Pancreatic Glucagon-like Peptide-1 Receptor.
Thorens et al., Diabetes 42(11):1678-1682 (Nov. 1, 1993): Cloning and Functional Expression of the Human Islet GLP-1 Receptor Demonstration that Exendin-4 is an Agonist and Exe.
Vertongen et al., Endocrinology 135(4):1537-1542 (Oct. 1, 1994): Ptiuitary Adenylate cyclase-activating polypeptide receptors of types I and II and glucaton-like peptide-1 rece.

*Primary Examiner* — Gyan Chandra
(74) *Attorney, Agent, or Firm* — Womble Carlyle Sandridge & Rice, LLP; Mark Pino; Alireza Behrooz

(57) ABSTRACT

Provided herein are cell-based bioassays for measuring GLP-I receptor agonist activity of test compounds, such as GLP-I receptor agonist compounds. Exemplary GLP-I receptor agonist compounds include exendins, exendin analogs, GLP-1(7-37), and GLP-1(7-37) analogs. The bioassays are useful for quantitatively determining cAMP generated in samples containing GLP-I receptor agonist compounds (e.g., exenatide) and 6-23 (clone 6) cells having GLP-I receptors, whereby the amount of cAMP generated can be correlated to the GLP-I receptor agonist activity of the GLPI receptor agonist compounds (e.g., exenatide). Suitable cell-based bioassays include enzyme-linked immunosorbent assays and homogeneous time-resolved fluorescence assays.

20 Claims, 3 Drawing Sheets

GLP-1 RECEPTOR AGONIST BIOASSAY

CROSS-REFERENCES TO RELATED APPLICATIONS

This application is a continuation of U.S. application Ser. No. 12/990,693, filed Dec. 14, 2010, which in turn is a national stage of PCT/US09/44135, filed May 15, 2009, which claims priority to U.S. Application No. 61/055,842 filed May 23, 2008, the disclosure of each of which is incorporated herein by reference.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 92494-853521_ST25.txt, created on Oct. 2, 2012, 27,860 bytes, machine format IBM-PC, MS-Windows operating system, is hereby incorporated by reference in its entirety for all purposes.

FIELD

The disclosure relates to cell-based assays for GLP-1 receptor agonist compounds.

BACKGROUND

Cell-based assay or bioassay development can range from cytotoxic assays, including apoptosis, to cell proliferation and metabolic assays. Cell-based assay development can also include high throughput screening assays and other custom bioassays used to characterize drug stability for GLP and GMP lot release, drug potency, and for drug purification and production support. Mechanisms of action, such as receptor binding, receptor activation, cell signaling, drug internalization and subcellular localization can be delineated in cell-based assays following treatment with drug compounds of interest. Bioassay development can encompass testing of conditioned medium, cell lysates or whole cells in a variety of formats including ELISA and immunohistochemical methods.

Exendin-4 (HGEGTFTSDLSKQMEEEAVR-LFIEWLKNGGPSSGAPPPS-NH$_2$ (SEQ ID NO:1)) is a peptide found in the saliva of the Gila monster, *Heloderma suspectum*; and exendin-3 (HSDGTFTSDLSKQMEEEAVR-LFIEWLKNGGPSSGAPPPS-NH$_2$ (SEQ ID NO:2)) is a peptide found in the saliva of the beaded lizard, *Heloderma horridum*. Exendins have some amino acid sequence similarity to some members of the glucagon-like peptide (GLP) family. For example, exendin-4 has about 53% sequence identity with glucagon-like peptide-1(GLP-1)(7-37) (HAEGTFTSDVSSYLEGQAAKEFIAWLVKGRG (SEQ ID NO:22)). However, exendin-4 is transcribed from a distinct gene, not the Gila monster homolog of the mammalian proglucagon gene from which GLP-1 is expressed. Additionally, exendin-4 is not an analog of GLP-1(7-37) because the structure of synthetic exendin-4 peptide was not created by sequential modification of the structure of GLP-1. Nielsen et al, *Current Opinion in Investigational Drugs*, 4(4):401-405 (2003).

Synthetic exendin-4, also known as exenatide, is commercially available as BYETTA® (Amylin Pharmaceuticals, Inc. and Eli Lilly and Company). BYETTA® contains exenatide, a preservative (e.g., metacresol), a tonicity-adjusting agent (e.g., mannitol), and a buffer (e.g., an acetate buffer). A once weekly formulation of exenatide is currently in development and is described in WO 2005/102293, the disclosure of which is incorporated by reference herein. This once weekly formulation comprises exenatide and biodegradable polymeric (e.g., poly(lactide-co-glycolide)) microspheres, and is referred to herein as EQW (Amylin Pharmaceuticals, Inc., Eli Lilly and Company, Alkermes, Inc.).

There is a need in the art for new and improved bioassays for determining the potency and activity of pharmaceutical compositions containing GLP-1 receptor agonist compounds, such as BYETTA®, and for determining the potency and activity of GLP-1 receptor agonist compounds, such as exenatide. Cell-based bioassays that meet these needs are described herein.

SUMMARY

Provided herein are bioassays useful for quantitatively measuring cyclic adenosine 3'5'-monophosphate (cAMP) generated by the interaction of GLP-1 receptor agonist compounds (or compositions comprising GLP-1 receptor agonist compounds) and 6-23 (clone 6) cells having functional GLP-1 receptors. The amount of cAMP generated by this interaction correlates to the GLP-1 receptor agonist activity of the GLP-1 receptor agonist compounds.

Provided herein are bioassays useful for quantitatively measuring cyclic adenosine 3'5'-monophosphate (cAMP) generated by the interaction of a test compound (that may or may not have GLP-1 receptor agonist activity) and 6-23 (clone 6) cells having functional GLP-1 receptors. The amount of cAMP generated by the interaction correlates to the GLP-1 receptor agonist activity of the test compound. This bioassay is useful for determining the GLP-1 receptor binding activity of a known or unknown compound relative to a standard, such as exenatide. In one embodiment, the test compound may be a component in a composition.

Provided herein are methods for detecting or measuring GLP-1 receptor agonist activity of a compound by preparing a sample containing (i) a test compound or a composition comprising a test compound and (ii) 6-23 (clone 6) cells; quantitatively measuring cAMP in the sample using a cell-based assay, and correlating the amount of cAMP to the GLP-1 receptor agonist activity of the test compound. Exemplary cell-based assays include enzyme-linked immunosorbent assays and homogeneous time-resolved fluorescence assays. In one embodiment, the test compound is a GLP-1 receptor agonist compound. In one embodiment, the GLP-1 receptor agonist compound is exenatide. In one embodiment, the composition comprising a test compound is BYETTA® or EQW.

Provided herein are methods for detecting or measuring GLP-1 receptor agonist activity of a compound by preparing a sample containing a GLP-1 receptor agonist compound and 6-23 (clone 6) cells; forming a reaction mixture by combining the preceding sample, a compound comprising an anti-cAMP antibody; and a compound comprising a labeled cAMP; quantitatively measuring cAMP in the sample, and correlating the amount of cAMP to the GLP-1 receptor agonist activity of the GLP-1 receptor agonist compound. In one embodiment, the compound comprising an anti-cAMP antibody is a compound comprising an antibody anti-cAMP monoclonal antibody labeled with a detectable moiety (e.g., a fluorescent moiety). In one embodiment, the sample is a composition, such as a pharmaceutical composition. In one embodiment, the GLP-1 receptor agonist compound is exenatide. In one embodiment, the sample is BYETTA® or EQW.

Provided herein are methods for detecting or measuring GLP-1 receptor agonist activity of a compound by preparing a sample containing (i) a GLP-1 receptor agonist compound; (ii) 6-23 (clone 6) cells; and (iii) a compound comprising a labeled cAMP; forming a reaction mixture by combining the preceding sample and a compound comprising an anti-cAMP antibody; quantitatively measuring cAMP in the sample; and correlating the amount of cAMP to the GLP-1 receptor agonist activity of the GLP-1 receptor agonist compound. In one embodiment, the compound comprising an anti-cAMP antibody is a compound comprising an anti-cAMP monoclonal antibody labeled with a detectable moiety (e.g., a fluorescent moiety). In one embodiment, the sample is a composition, such as a pharmaceutical composition. In one embodiment, the GLP-1 receptor agonist compound is exenatide. In one embodiment, the sample is BYETTA® or EQW.

Provided herein are methods for detecting or measuring GLP-1 receptor agonist activity of a compound by preparing a sample containing a GLP-1 receptor agonist compound and 6-23 (clone 6) cells; forming a reaction mixture by combining: the preceding sample, a first compound comprising an anti-cAMP antibody (e.g., monoclonal antibody) linked to a rare earth cryptate or a rare earth chelate, and a second compound comprising a fluorescently-labeled cAMP; irradiating the reaction mixture; quantitatively determining the presence or amount of cAMP in the sample; and correlating the amount of cAMP to the GLP-1 receptor agonist activity of the GLP-1 receptor agonist compound. In one embodiment, the rare earth cryptates and chelates are selected from terbium cryptate, europium cryptate, dysprosium cryptate, samarium cryptate, neodymium cryptate, terbium chelate, europium chelate, dysprosium chelate, samarium chelate, and neodymium chelate. In one embodiment, the sample is a composition, such as a pharmaceutical composition. In one embodiment, the GLP-1 receptor agonist compound is exenatide. In one embodiment, the sample is BYETTA® or EQW.

Provided herein are methods for detecting or measuring GLP-1 receptor agonist activity of a compound by preparing a sample comprising a GLP-1 receptor agonist compound, 6-23 (clone 6) cells, and a compound comprising a fluorescently-labeled cAMP; forming a reaction mixture by combining the preceding sample and a compound comprising an anti-cAMP antibody (e.g., monoclonal antibody) linked to a rare earth cryptate or a rare earth chelate; irradiating the reaction mixture; quantitatively determining the presence or amount of cAMP in the sample; and correlating the amount of cAMP to the GLP-1 receptor agonist activity of the GLP-1 receptor agonist compound. In one embodiment, the sample is a composition, such as a pharmaceutical composition. In one embodiment, the GLP-1 receptor agonist is exenatide. In one embodiment, the sample is BYETTA® or EQW.

Provided herein are methods for detecting or measuring GLP-1 receptor agonist activity of a compound by preparing a sample comprising a GLP-1 receptor agonist compound and 6-23 (clone 6) cells; adding an agent to stimulate the preceding sample to generate the production of cAMP in the 6-23 (clone 6) cells; forming a reaction mixture by combining the preceding stimulated sample, a first compound comprising an anti-cAMP monoclonal antibody linked to Europium-cryptate capable of generating emitted fluorescence at a measuring wavelength of about 620 nm; and a second compound comprising cAMP linked to a fluorescent moiety capable of emitting fluorescence at a correcting wavelength of about 665 nm; irradiating the reaction mixture from step (c) at a single excitation wavelength of about 337 nm by an external radiation source; simultaneously measuring both the emitted fluorescence at about 620 nm and the emitted fluorescence at about 665 nm which takes account interference parameters of the reaction mixture; calculating the corrected fluorescence for the fluorescence emitted by the first compound at about 620 nm based on the fluorescence emitted by the second compound at about 665 nm; correlating the corrected fluorescence reading to the presence or quantitative amount of cAMP in the sample; and correlating the amount of cAMP to the GLP-1 receptor agonist activity of the GLP-1 receptor agonist compound. In one embodiment, the reaction mixture comprises a buffer that can lyse the 6-23 (clone 6) cells. In one embodiment, the sample is a composition, such as a pharmaceutical composition. In one embodiment, the GLP-1 receptor agonist compound is exenatide. In one embodiment, the sample is BYETTA® or EQW.

Provided herein are methods for detecting or measuring GLP-1 receptor agonist activity of a compound by preparing a sample comprising a GLP-1 receptor agonist compound; 6-23 (clone 6) cells; and a compound comprising cAMP linked to a fluorescent moiety capable of emitting fluorescence at a correcting wavelength of about 665 nm; adding an agent to stimulate the preceding sample to generate cAMP in the 6-23 (clone 6) cells; forming a reaction mixture by combining the preceding stimulated sample and a compound comprising an anti-cAMP monoclonal antibody linked to Europium-cryptate capable of generating emitted fluorescence at a measuring wavelength of about 620 nm; irradiating the reaction mixture at a single excitation wavelength of about 337 nm by an external radiation source; simultaneously measuring both the emitted fluorescence at about 620 nm and the emitted fluorescence at about 665 nm which takes account interference parameters of the reaction mixture; calculating a corrected fluorescence for the fluorescence emitted by the compound at about 620 nm based on the fluorescence emitted by the compound at about 665 nm; correlating the corrected fluorescence reading to the presence or quantitative amount of cAMP in the sample; and correlating the amount of cAMP to the GLP-1 receptor agonist activity of the GLP-1 receptor agonist compound. In one embodiment, the reaction mixture comprises a buffer capable of lysing the 6-23 (clone 6) cells. In one embodiment, the sample is a composition, such as a pharmaceutical composition. In one embodiment, the GLP-1 receptor agonist compound is exenatide. In one embodiment, the sample is BYETTA® or EQW.

The GLP-1 receptor agonist activity of the GLP-1 receptor agonist compound (e.g., exenatide) can be used in documents submitted to a government agency (e.g., the United States Food and Drug Administration), and can also be used in supporting documentation for GLP compliance, GMP compliance, and quality control. The quantitative results can further be used to optimize manufacturing processes, and the steps for obtaining the quantitative results can be used to prepare standard operating procedures (SOPs).

DETAILED DESCRIPTION

Figure 1:
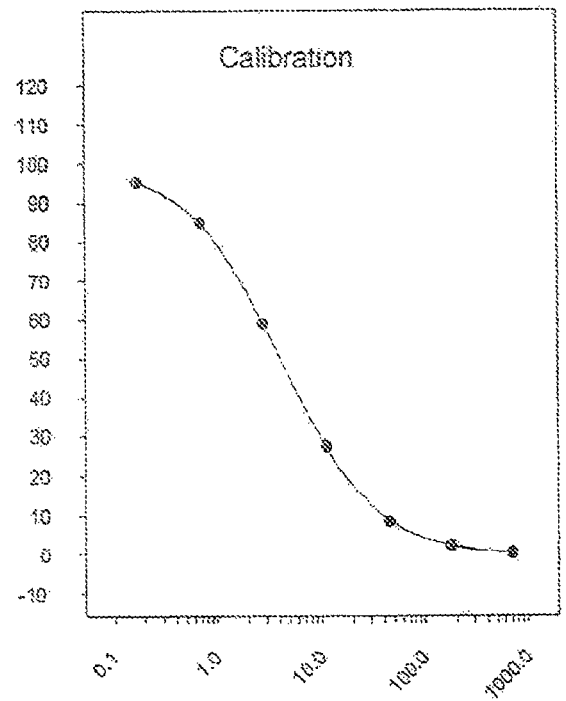
FIG. 1 is the bioassay calibration standard for exenatide as prepared following the methods described in the Examples.

It has been unexpectedly discovered that cell-based assays using the rMTC6-23 (clone 6) cell line provide superior results for determining the GLP-1 receptor agonist activity of a compound (e.g., known test compounds, unknown test compounds, GLP-1 receptor agonist compounds) based on the cAMP potency and activity generated in the cell-based assay when compared to the use of other cell lines having GLP-1 receptors or to cell membranes having GLP-1 receptors where the membranes are harvested from living cells.

Because of the unexpectedly superior signals produced for cAMP potency and activity, which are correlated to GLP-1 receptor agonist activity, using the 6-23 (clone 6) cell line in cell-based assays for GLP-1 receptor agonist compounds, the results showing the GLP-1 receptor agonist activity of the compound are useful for making analogs of known GLP-1 receptor agonist compounds; in preparing documents for submission to government regulatory agencies (e.g., the U.S. Food and Drug Administration); for preparing supporting documentation to demonstrate GLP compliance, GMP compliance, and quality control; and to optimize manufacturing processes for GLP-1 receptor agonist compounds (e.g., exenatide).

In one embodiment of the bioassays described herein, the GLP-1 receptor agonist activity of a compound is quantitatively determined by correlations to cAMP production in cell-based assays with 6-23 (clone 6) cells. The cell-based assay uses living 6-23 (clone 6) cells. The cell-based assay does not use cell membranes that have been harvested from living 6-23 (clone 6) cells. The 6-23 (clone 6) cells are available from the American Type Culture Collection as ATCC® No. CRL-1607™ and the European Collection of Cell Cultures as ECACC No. 87042206.

In the methods described herein, the cell-based assay can be any known in the art. In one embodiment, the cell-based assay is an enzyme-linked immunosorbent assay (ELISA). ELISA kits are commercially available from numerous sources, such as Cell Sciences® (Canton, Mass.). Methods for using ELISA kits are known in the art and the kits generally include instruction manuals, e.g., on how to prepare samples, standards, calibration curves, and conduct experiments. In another embodiment, the cell-based assay is a homogeneous time-resolved fluorescence assay (HTRF®). HTRF® kits are commercially available from Cisbio International (Bedford, Mass.). Methods for using HTRF® kits are known in the art and the kits generally include instruction manuals, e.g., on how to prepare samples, standards, calibration curves, and conduct experiments. Homogeneous time-resolved fluorescence cell-based assays are described in U.S. Pat. No. 5,527,684, the disclosure of which is incorporated by reference herein, and Document Reference No. 62AM4PEB rev02 (August 2007) available from Cisbio HTRF®Product Center. See www.htrf.com/products/gpcr/camp/, the disclosure of which is incorporated by reference herein.

A stimulating agent can optionally be used in the methods described herein to increase the production of cAMP in the 6-23 (clone 6) cells when they are combined with the test compound or the GLP-1 receptor agonist compound (e.g., exenatide). Exemplary stimulating agents include forskolin, antidiuretic hormone (ADH), prostaglandins (e.g., PGE1, PGE2), phosphate diesterase inhibitors (e.g., such as cyclic nucleotide phosphodiesterase inhibitors), and the like. An exemplary cyclic nucleotide phosphodiesterase inhibitor is IBMX (isobutylmethylxanthine). IBMX increases cAMP and cGMP production cells. IBMX is commercially available from Sigma (Catalog No. 17018).

A buffer comprising a lysing agent can optionally be used in the methods described herein to measure the cAMP activity produced by the 6-23 (clone 6) cells. Exemplary lysis buffers comprise tris-HCl, ethylenediaminetetraacetic acid (EDTA), ethylene glycol tetraacetic acid (EGTA), sodium dodecyl sulfate (SDS), sodium deoxycholate, octylphenolpoly-(ethyleneglycol-ether)$_x$ (Triton-X), nonyl phenoxypolyethoxylethanol (NP-40), or a combination of two or more thereof. An exemplary lysis buffer solution is buffer P2 which contains SDS, which is believed to puncture holes in cellular membranes to lyse the cells.

A "GLP-1 receptor agonist compound" refers to compounds having GLP-1 receptor activity. Such exemplary compounds include exendins, exendin analogs, exendin agonists, GLP-1(7-37), GLP-1(7-37) analogs, GLP-1(7-37) agonists, and the like.

The term "exendin" includes naturally occurring (or synthetic versions of naturally occurring) exendin peptides that are found in the salivary secretions of the Gila monster. Exendins of particular interest include exendin-3 and exendin-4. The exendins, exendin analogs, and exendin agonists for use in the methods described herein may optionally be amidated, and may also be in an acid form, pharmaceutically acceptable salt form, or any other physiologically active form of the molecule.

"Exendin analog" refers to peptides or other compounds which elicit a biological activity of an exendin reference peptide, preferably having a potency equal to or better than the exendin reference peptide (e.g., exendin-4), or within five orders of magnitude (plus or minus) of potency compared to the exendin reference peptide, when evaluated by art-known measures such as receptor binding and/or competition studies as described, e.g., by Hargrove et al, *Regulatory Peptides,* 141:113-119 (2007), the disclosure of which is incorporated by reference herein. Preferably, the exendin analogs will bind in such assays with an affinity of less than 1 μM, and more preferably with an affinity of less than 3 nM, or less than 1 nM. The term "exendin analog" may also be referred to as "exendin agonist".

Exendin analogs also include the peptides described herein which have been chemically derivatized or altered, for example, peptides with non-natural amino acid residues (e.g., taurine, β-amino acid residues, γ-amino acid residues, and D-amino acid residues), C-terminal functional group modifications, such as amides, esters, and C-terminal ketone modifications and N-terminal functional group modifications, such as acylated amines, Schiff bases, or cyclization, as found, for example, in the amino acid pyroglutamic acid. Exendin analogs may also contain other chemical moieties, such as peptide mimetics.

Exemplary exendins and exendin analogs exendin-4 (SEQ ID NO:1); exendin-3 (SEQ ID NO:2); Leu$^{14}$-exendin-4 (SEQ ID NO:3); Leu$^{14}$,Phe$^{25}$-exendin-4 (SEQ ID NO:4); Leu$^{14}$, Ala$^{19}$,Phe$^{25}$-exendin-4 (SEQ ID NO:5); exendin-4(1-30) (SEQ ID NO:6); Leu$^{14}$-exendin-4(1-30) (SEQ ID NO:7); Leu$^{14}$,Phe$^{25}$-exendin-4(1-30) (SEQ ID NO:8); Leu$^{14}$,Ala$^{19}$, Phe$^{25}$-exendin-4(1-30) (SEQ ID NO:9); exendin-4(1-28) (SEQ ID NO:10); Leu$^{14}$-exendin-4(1-28) (SEQ ID NO:11); Leu$^{14}$,Phe$^{25}$-exendin-4(1-28) (SEQ ID NO:12); Leu$^{14}$,Ala$^{19}$, Phe$^{25}$-exendin-4 (1-28) (SEQ ID NO:13); Leu$^{14}$,Lys$^{17,20}$, Ala$^{19}$,Glu$^{21}$,Phe$^{25}$,Gln$^{28}$-exendin-4 (SEQ ID NO:14); Leu$^{14}$, Lys$^{17,20}$,Ala$^{19}$,Glu$^{21}$,Gln$^{28}$-exendin-4 (SEQ ID NO:15); octylGly$^{14}$,Gln$^{28}$-exendin-4 (SEQ ID NO:16); Leu$^{14}$,Gln$^{28}$, octylGly$^{34}$-exendin-4 (SEQ ID NO:17); Phe$^{4}$,Leu$^{14}$,Gln$^{28}$, Lys$^{33}$,Glu$^{34}$, Ile$^{35,36}$,Ser$^{37}$-exendin-4(1-37) (SEQ ID NO:18); Phe$^{4}$,Leu$^{14}$,Lys$^{17,20}$,Ala$^{19}$,Glu$^{21}$,Gln$^{28}$-exendin-4 (SEQ ID NO:19); Val$^{11}$,Ile$^{13}$,Leu$^{14}$,Ala$^{16}$,Lys$^{21}$,Phe$^{25}$-exendin-4 (SEQ ID NO:20); exendin-4-Lys$^{40}$ (SEQ ID NO:21); lixisenatide (Sanofi-Aventis/Zealand Pharma); CJC-1134 (ConjuChem, Inc.); [N$^{\epsilon}$-(17-carboxyheptadecanoic acid) Lys$^{20}$]exendin-4-NH$_2$; [N$^{\epsilon}$-(17-carboxyhepta-decanoyl) Lys$^{32}$]exendin-4-NH$_2$; [desamino-His$^{1}$,N$^{\epsilon}$-(17-carboxyheptadecanoyl)Lys$^{20}$]exendin-4-NH$_2$; [Arg$^{12,27}$, NLe$^{14}$,N$^{\epsilon}$-(17-carboxy-heptadecanoyl)Lys$^{32}$]exendin-4-NH$_2$; [N$^{\epsilon}$-(19-carboxy-nonadecanoylamino)Lys$^{20}$]-exendin-4-NH$_2$; [N$^{\epsilon}$-(15-carboxypentadecanoylamino)Lys$^{20}$]-exendin-4-NH$_2$; [N$^{\epsilon}$-(13-carboxytridecanoylamino)Lys$^{20}$]exendin-4-NH$_2$; [N$^{\epsilon}$-(11-carboxy-undecanoyl-amino)Lys$^{20}$]exendin-4-NH$_2$; exendin-4-Lys$^{40}$($\epsilon$-MPA)-NH$_2$; exendin-4-Lys$^{40}$ ($\epsilon$-AEEA-AEEA-MPA)-NH$_2$; exendin-4-Lys$^{40}$($\epsilon$-AEEA-MPA)-NH$_2$; exendin-4-Lys$^{40}$($\epsilon$-MPA)-albumin; exendin-4-Lys$^{40}$($\epsilon$-AEEA-AEEA-MPA)-albumin; exendin-4-Lys$^{40}$($\epsilon$-AEEA-MPA)-albumin; and the like. AEEA refers to [2-(2-amino) ethoxy)]ethoxy acetic acid. EDA refers to ethylenediamine. MPA refers to maleimidopropionic acid. The exendins and exendin analogs may optionally be amidated.

Other exendins and exendin analogs useful in the methods described herein include those described in WO 98/05351; WO 99/07404; WO 99/25727; WO 99/25728; WO 99/40788; WO 00/41546; WO 00/41548; WO 00/73331; WO 01/51078; WO 03/099314; U.S. Pat. No. 6,956,026; U.S. Pat. No. 6,506,724; U.S. Pat. No. 6,703,359; U.S. Pat. No. 6,858,576; U.S. Pat. No. 6,872,700; U.S. Pat. No. 6,902,744; U.S. Pat. No. 7,157,555; U.S. Pat. No. 7,223,725; U.S. Pat. No. 7,220,721; US Publication No. 2003/0036504; and US Publication No. 2006/0094652, the disclosures of which are incorporated by reference herein in their entirety.

"GLP-1(7-37) analogs" refers to peptides or other compounds which elicit a biological activity similar to that of GLP-1(7-37), when evaluated by art-known measures such as receptor binding assays or in vivo blood glucose assays as described, e.g., by Hargrove et al, *Regulatory Peptides*, 141: 113-119 (2007), the disclosure of which is incorporated by reference herein. In one embodiment, the term "GLP-1(7-37) analog" refers to a peptide that has an amino acid sequence with 1, 2, 3, 4, 5, 6, 7 or 8 amino acid substitutions, insertions, deletions, or a combination of two or more thereof, when compared to the amino acid sequence of GLP-1(7-37). In one embodiment, the GLP-1(7-37) analog is GLP-1(7-36). GLP-1(7-37) analogs include the amidated forms, the acid form, the pharmaceutically acceptable salt form, and any other physiologically active form of the molecule.

Exemplary GLP-1(7-37) and GLP-1(7-37) analogs include GLP-1(7-37) (SEQ ID NO:22); GLP-1(7-36) (SEQ ID NO:23); liraglutide (VICTOZA® from Novo Nordisk); albiglutide (SYNCRIA® from Glaxo SmithKline); taspoglutide (Hoffman La-Roche); LY2189265 (Eli Lilly and Company); LY2428757 (Eli Lilly and Company); desamino-His$^{7}$,Arg$^{26}$,Lys$^{34}$(N$^{\epsilon}$-($\gamma$-Glu(N-$\alpha$-hexadecanoyl)))-GLP-1 (7-37); desamino-His$^{7}$, Arg$^{26}$,Lys$^{34}$(N$^{\epsilon}$-octanoyl)-GLP-1(7-37); Arg$^{26,34}$,Lys$^{38}$(N'-($\omega$-carboxypentadecanoyl))-GLP-1 (7-38); Arg$^{26,34}$,Lys$^{36}$ (N$^{\epsilon}$-($\gamma$-Glu(N-$\alpha$-hexadecanoyl)))-GLP-1(7-36); Aib$^{8,35}$,Arg$^{26,34}$,Phe$^{31}$-GLP-1(7-36)) (SEQ ID NO:24); HXaa$_8$EGTFTSDVSSYLEXaa$_{22}$Xaa$_{23}$ AAKEFIXaa$_{30}$WLXaa$_{33}$Xaa$_{34}$G Xaa$_{36}$Xaa$_{37}$; wherein Xaa$_8$ is A, V, or G; Xaa$_{22}$ is G, K, or E; Xaa$_{23}$ is Q or K; Xaa$_{30}$ is A or E; Xaa$_{33}$ is V or K; Xaa$_{34}$ is K, N, or R; Xaa$_{36}$ is R or G; and Xaa$_{37}$ is G, H, P, or absent (SEQ ID NO:25); Arg$^{34}$-GLP-1 (7-37) (SEQ ID NO:26); Glu$^{36}$-GLP-1(7-37) (SEQ ID NO:27); Lys$^{22}$-GLP-1(7-37) (SEQ ID NO:28); Gly$^{8,36}$, Glu$^{22}$-GLP-1(7-37) (SEQ ID NO:29); Val$^{8}$,Glu$^{22}$,Gly$^{36}$-GLP-1(7-37) (SEQ ID NO:30); Gly$^{8,36}$,Glu$^{22}$,Lys$^{33}$,Asn$^{34}$-GLP-1(7-37) (SEQ ID NO:31); Val$^{8}$,Glu$^{22}$,Lys$^{33}$,Asn$^{34}$, Gly$^{36}$-GLP-1(7-37) (SEQ ID NO:32); Gly$^{8,36}$,Glu$^{22}$,Pro$^{37}$-GLP-1(7-37) (SEQ ID NO:33); Val$^{8}$,Glu$^{22}$,Gly$^{36}$,Pro$^{37}$-GLP-1(7-37) (SEQ ID NO:34); Gly$^{8,36}$,Glu$^{22}$,Lys$^{33}$, Asn$^{34}$, Pro$^{37}$-GLP-1(7-37) (SEQ ID NO:35); Val$^{8}$,Glu$^{22}$,Lys$^{33}$, Asn$^{34}$,Gly$^{36}$,Pro$^{37}$-GLP-1(7-37) (SEQ ID NO:36); Gly$^{8,36}$, Glu$^{22}$-GLP-1(7-36) (SEQ ID NO:37); Val$^{8}$,Glu$^{22}$,Gly$^{36}$-GLP-1(7-36) (SEQ ID NO:38); Val$^{8}$,Glu$^{22}$,Asn$^{34}$,Gly$^{36}$-GLP-1(7-36) (SEQ ID NO:39); Gly$^{8,36}$,Glu$^{22}$,Asn$^{34}$-GLP-1 (7-36) (SEQ ID NO:40). Each of the GLP-1(7-37) and GLP-1(7-37) analogs may optionally be amidated.

In one embodiment, the GLP-1(7-37) or GLP-1(7-37) analogs are covalently linked (directly or by a linking group) to an Fc portion of an immunoglobulin (e.g., IgG, IgE, IgG, and the like). For example, any one of SEQ ID NOs:25-40 may be covalently linked to the Fc portion of an immunoglobulin comprising the sequence of: AESKYGPPCPPCPAPXaa$_{16}$ Xaa$_{17}$Xaa$_{18}$GGPSVFLFPPKPKDTLMISRTPEVTCVVVD VSQEDPEVQFNWYVDGVEVH NAKTKPREEQFXaa$_{80}$ STYRVVSVLTVLHQDWLNGKEYKCKVSNKGL PSS-IEKTISKAKGQPREPQVYTLPPSQEEMTKNQVSLT CLVKGFYPSDIAVEWESNGQPENNYKTTPPVLD SDGSFFLYSRLTVDKSRWQEGNVFSCS-VMHEALHNHYTQKSLSLSLGXaa$_{230}$; wherein Xaa$_{16}$ is P or E; Xaa$_{17}$ is F, V or A; Xaa$_{18}$ is L, E or A; Xaa$_{80}$ is N or A; and Xaa$_{230}$ is K or absent (SEQ ID NO:41). The linking group may be any chemical moiety (e.g., amino acids and/or chemical groups). In one embodiment, the linking group is (-GGGGS—)$_x$ (SEQ ID NO:42) where x is 1, 2, 3, 4, 5 or 6; preferably 2, 3 or 4; more preferably 3. In one embodiment, the GLP-1(7-37) analog covalently linked to the Fc portion of an immunoglobulin comprises the amino acid sequence: HGEGTFTSDVSSYLEEQAAKEFI-AWLVKGGGGGGGSGGGGSGGGGSA ESKYGPPCP-PCPAPEAAGGPSVELFPPKPKDTLMIS-RTPEVTCVVVDVSQEDPEVQ FNWYVDGVEVHNAKTKPREEQFNSTYRV-VSVLTVLHQDWLNGKEYKCKVSN KGLPSSIEK-TISKAKGQPREPQVYTLPPSQEEMTKN-QVSLTCLVKGFYPSDIAVEWESN GQPENNYKTTPPVLDSDGSFFLYSR-LTVDKSRWQEGNVFSCSVMHEALHNHYTQ KSLSLSLG (SEQ ID NO:43).

In another embodiment, the GLP-1(7-37) or GLP-1(7-37) analog may be covalently linked (directly or through a linking group) to one or two polyethylene glycol molecules. For example, a GLP-1(7-37) analog may comprise the amino acid sequence: HXaa$_8$EGTFTSDVSSYLEXaa$_{22}$QAAKEFIA WLXaa$_{33}$KGGPSSGAPPPC$_{45}$C$_{46}$—Z, wherein Xaa$_8$ is:

D-Ala, G, V, L, I, S or T; $Xaa_{22}$ is G, E, D or K; $Xaa_{33}$ is: V or I; and Z is OH or $NH_2$, (SEQ ID NO:44), and, optionally, wherein (i) one polyethylene glycol moiety is covalently attached to $C_{45}$, (ii) one polyethylene glycol moiety is covalently attached to $C_{46}$, or (iii) one polyethylene glycol moiety is attached to $C_{45}$ and one polyethylene glycol moiety is attached to $C_{46}$. In one embodiment, the GLP-1(7-37) analog is HVEGTFTSDVSSYLEEQAAKEFIAWLIKGGP SSGAPPPC$_{45}$C$_{46}$-NH$_2$ (SEQ ID NO:45) and, optionally, wherein (i) one polyethylene glycol moiety is covalently attached to $C_{45}$, (ii) one polyethylene glycol moiety is covalently attached to $C_{46}$, or (iii) one polyethylene glycol moiety is attached to $C_{45}$ and one polyethylene glycol moiety is attached to $C_{46}$.

In one embodiment, the GLP-1 receptor agonist compounds are in a single pharmaceutical composition with another therapeutic agent. Such therapeutic agents include small molecules (e.g., antidiabetic agents, antiobesity agents, antihypertensive agents) and peptides such as amylin, amylin analogs, PYY, PYY analogs, GIP, GIP analogs, leptin, leptin analogs, and the like. Pharmaceutical compositions containing two or more active ingredients may be used in the bioassays described herein for measuring the GLP-1 receptor binding activity of the GLP-1 receptor agonist compound. The additional active ingredients in the pharmaceutical compositions should not interfere with the bioassay.

In one embodiment, the GLP-1 receptor agonist compounds are linked to another peptide (e.g., amylin, amylin analogs, PYY, PYY analogs, GIP, GIP analogs, leptin, leptin analogs, and the like) to form a hybrid peptide. Hybrid peptides comprising GLP-1 receptor agonist compounds and another therapeutic peptide are described, for example, in WO 2005/077072 and WO 2007/022123, the disclosures of which are incorporated by reference herein. The hybrid peptides may be used in the bioassays described herein for measuring the GLP-1 receptor binding activity of that portion of the hybrid peptide that contains the GLP-1 receptor agonist compound. The hybrid peptide, a portion of which does not have GLP-1 receptor binding activity, should not interfere with the bioassay.

In one embodiment, GLP-1 receptor agonist compounds may be linked to one or more polymers, such as polyethylene glycols, polyamino acids, fatty acids, albumin, immunoglobulins, immunoglobulin Fc fragments, and the like. The polymer linked to the GLP-1 receptor agonist compound should not interfere with the ability of the bioassay to measure the GLP-1 receptor binding activity of the compound.

The GLP-1 receptor agonist compounds may be present in the form of pharmaceutical compositions for use in the bioassays described herein. Such pharmaceutical compositions are known in the art and described, e.g., in U.S. Pat. No. 7,521,423; U.S. Pat. No. 7,456,254; WO 2000/037098; WO 2005/021022; WO 2005/102293; WO 2006/068910; WO 2006/125763; WO 2009/068910; US Publication No 2004/0106547; and the like, the disclosures of which are incorporated herein by reference.

GLP-1 receptor agonist compounds may be prepared by processes well known in the art, e.g., peptide purification as described in Eng et al, *J. Biol. Chem.*, 265:20259-62 (1990); standard solid-phase peptide synthesis techniques as described in Raufman et al, *J. Biol. Chem.*, 267:21432-37 (1992); recombinant DNA techniques as described in Sambrook et al, Molecular Cloning: A Laboratory Manual, 2d Ed., Cold Spring Harbor (1989); and the like.

EXAMPLES

The following examples are presented to more fully explain the disclosure. These examples are for illustrative purposes only and are not intended to limit the disclosure or claims.

Example 1

The bioassays were prepared and run as described herein. Rat thyroid carcinoma 6-23 (clone 6) cells were obtained for use in the cell-based assay. The test compounds and compositions included exenatide; BYETTA®; and EQW. The reference standard was exenatide. Cell-based assays were performed using the HTRF® cAMP dynamic 2 1,000 assay kit, available from Cisbio as Catalog No. 62AM4PEB.

The HTRF® standards and calibrations were prepared following the instructions in the kit. In particular, the HTRF® calibration standard, the HTRF® cAMP calibration control, the cell noise, the HTRF® negative control, the HTRF® positive control were prepared. Testing was conducted using forskolin to confirm the cAMP activity of the 6-23 (clone 6) cells.

The exenatide test sample was prepared as a solution of approximately 60 μM exenatide in 30 mM acetate buffer (at a pH of about 4.5), which was equivalent to about 0.25 mg/mL exenatide. The exenatide test sample was equilibrated to room temperature and vortexed for 60 seconds. The exenatide test sample was diluted 1:100, 1:10, and 1:6.

The BYETTA® test sample, containing 250 μg/mL exenatide, was diluted 1:100, 1:10, and 1:6.

EQW is manufactured as a dry drug product. The EQW sample was prepared as follows: 50 mg±5 mg of the dry exenatide product was placed in a 20 mL scintillation vial, followed by the addition of 10 mL of a solution containing 20% acetic acid in dimethyl sulfoxide (DMSO). The scintillation vial was placed in a floating rack in a sonication bath filled with ambient water and was sonicated for 20 minutes. The resulting solution contained exenatide at a concentration of 60 μM. Thereafter, the EQW test sample was diluted to 1:100, 1:10, and 1:6.

The 6-23 (clone 6) cells were obtained from the cell culture lab in a flat vessel. The cells were detached using 5 mL of ethylenediaminetetraacetic acid (EDTA). For example, 5 mL EDTA was added to the opposite side of the cells to pre-rinse. The vessel was rocked so that the EDTA solution came into contact with the entire surface of the cell monolayer. The solution was aspirated. A new 5 mL aliquot of EDTA was added to the cell surface monolayer using a 5 mL serological pipette and incubated at room temperature for about 5-11 minutes. The cells were dislodged by tapping the sides of the flat vessel. A pipette was used to actuate the cells. The cell mixture was transferred to a flask and 5 mL HEPES-BCM solution was added thereto. The cells were rinsed and then centrifuged at 1000 rpm for 5 minutes. The cell pellet was removed and actuated. The cell count was about $3.00 \pm 2.00 \times 10^6$ cells per mL The cells were diluted to a target concentration of about $4.00 \pm 0.25 \times 10^5$ cell/ml and placed in a 4.5 mL stimulation buffer comprising IBMX.

The HEPES-BCM solution was prepared as follows: 1666 μL of 30% bovine serum albumin (BSA) (Amresco Catalog No. K719-50 ml) was added to a 500 mL Hank's Buffered Salt Solution (HBSS) container. The HBSS/BSA preparation was stirred at room temperature. HEPES buffer was added to the HBSS/BSA preparation to a HEPES concentration of 5 mM. The pH of the preparation was adjusted to 7.40 using aqueous 1N NaOH. The solution was then filtered with a 0.22 µm membrane filter.

The exenatide test samples (i.e., exenatide, BYETTA®, EQW) were prepared and run as follows: (1) a solution containing 25 µL the exenatide test sample and a cAMP-fluorescent dye conjugate was added to the wells; (2) 25 µL of the 6-23 (clone 6) cell solution was added to the wells; (3) the combined solutions were incubated for 30±2 minutes at room temperature; (4) 50 µL Eu-labeled antibody preparation in a lysis buffer was added to the wells; and (5) the result was read in an HTRF® capable plate reader.

The exenatide reference samples were prepared as a standard and run as follows: (1) a solution containing 25 µL exenatide and cAMP-fluorescent dye conjugate was added to the wells; (2) 25 µL of the 6-23 (clone 6) cell solution was added to the wells; (3) the combined solutions were incubated for 30±2 minutes at room temperature; (4) 50 µL Eu-labeled antibody preparation in a lysis buffer was added to the wells; (5) the mixture was incubated for 60 minutes; and (6) the result was read in an HTRF® capable plate reader. The purpose of preparing the exenatide reference samples was to show that at known concentrations (e.g., known dilutions of the exenatide reference standard) of exenatide in any solution the bioassay measured the percent exenatide content as a fraction of the content of the reference standard. Fractions above 100% indicated higher exenatide contents, and fractions below 100% indicated lower exenatide contents compared to the reference standard.

The negative control (no FRET) was prepared and run as follows: (1) 50 µL HEPES-BCM containing 6-23 (clone 6) cells and exenatide was added to the wells; (2) the solution in the wells were incubated for 30±2 minutes at room temperature; (3) 50 µL Eu-labeled antibody preparation was added to the wells; (4) the mixture was incubated for at least 60 minutes; and (5) the results were read in an HTRF® capable plate reader.

The calibration standard was a sample of a known amount of cAMP and was used in eight different concentrations to correlate the fluorescent response to the concentration of cAMP. In this case the calibration was used to confirm that the HTRF® kit conformed to the manufacturer's specifications. The calibration standard was prepared and run as follows: (1) 25 of each standard was added to the wells; (2) 25 µL stimulation buffer containing IBMX was added to the wells; (3) the combined solutions were incubated for 30±2 minutes at room temperature; (4) 50 µL Eu-labeled antibody preparation in a lysis buffer was added to the wells; (5) the mixture was incubated for 60 minutes; and (6) the results were read in an HTRF® capable plate reader. The calibration standard is presented in FIG. 1.

The HTRF® positive control (maximum FRET) was prepared and run as follows: (1) 25 µL HEPES-BCM containing 6-23 (clone 6) cells, exenatide, and cAMP-fluorescent dye conjugate was added to the wells; (2) 25 µL stimulation buffer containing IBMX was added to the wells; (3) the combined solutions in the wells were incubated for 30±2 minutes at room temperature; (3) 50 µL Eu-labeled antibody preparation in a lysis buffer was added to the wells; (4) the mixture was incubated for at least 60 minutes; and (5) the results were read in an HTRF® capable plate reader.

The cell noise solution (positive control and 6-23 (clone 6) cells) was prepared and run as follows: (1) 25 µL HEPES-BCM solution containing 6-23 (clone 6) cells and cAMP-fluorescent dye conjugate was added to the wells; (2) 25 µL stimulation buffer containing IBMX was added to the wells; (3) the combined solutions in the wells were incubated for 30±2 minutes at room temperature; (3) 50 µL Eu-labeled antibody preparation in a lysis buffer was added to the wells; (4) the mixtures were incubated for 60 minutes; and (5) the results were read in an HTRF® capable plate reader.

The forskolin solution was prepared and run as follows: (1) 25 µL forskolin in HEPES-BCM solution was added to the wells; (2) 25 µL of the 6-23 (clone 6) cell solution was added to the wells; (3) the combined solutions in the wells were incubated for 30±2 minutes at room temperature; (4) 50 µL Eu-labeled antibody preparation was added to the wells; (5) the mixtures were incubated for 60 minutes; and (6) the results were read in an HTRF® capable plate reader.

The data was collected from each well of the 96-well plate as fluorescence intensity data at 620 nm and 665 nm, respectively. The fluorescence intensity at 665 nm over the fluorescence intensity at 620 nm was calculated according to the following equation:

$$\text{Ratio} = \frac{A_{665\ nm}}{A_{620\ nm}} \times 10^4.$$

The average value for the negative control was calculated according to the following equation:

$$HTRF\ \text{Negative Control Average Ratio} = \frac{\sum_{1}^{n} \text{Ratio negative control}}{n}.$$

The ratios were corrected against the HTRF® negative control according to the following equation:

$$\text{Delta } F = \frac{\text{Ratio} - \text{Ratio } HTRF\ \text{negative control}}{\text{Ratio } HTRF\ \text{negative control}} \times 100.$$

This data transformation provided values that were plate reader independent. Delta F was expected to be a better measure across different brands and technologies of time resolved fluorescence instrument platforms. The Delta F for each well was calculated.

Delta F was then divided over the maximum signal, Delta F max, generated in the absence of cAMP to give a normalized ratio of signal compared to the maximum signal generated during the assay according to the formula:

$$\frac{\text{Delta } F}{\text{Delta}F_{max}} = \frac{\text{Ratio(sample)} - RatioHTRFneg\ \text{control}}{\text{Ratio(buffer)} - RatioHTRFneg\ \text{control}} \times 100.$$

For a set of replicate measurements, the average ratio was computed according to the formula:

$$\frac{\text{Average } DeltaF}{DeltaF_{max}} = \frac{\sum_{1}^{n} \frac{DeltaF}{DeltaF_{max}}}{n}.$$

The standard deviation was computed according to the formula:

$$SD = \sqrt{\frac{\sum_{1}^{n}(\text{Ratio} - \text{Average Ratio})^2}{n-1}}.$$

The % CV was computed according to the formula:

$$\% \ CV = \frac{SD}{\text{Average Ratio}} \times 100.$$

Example 2

Analysis of Exenatide as Reference and Test

Figure 2:
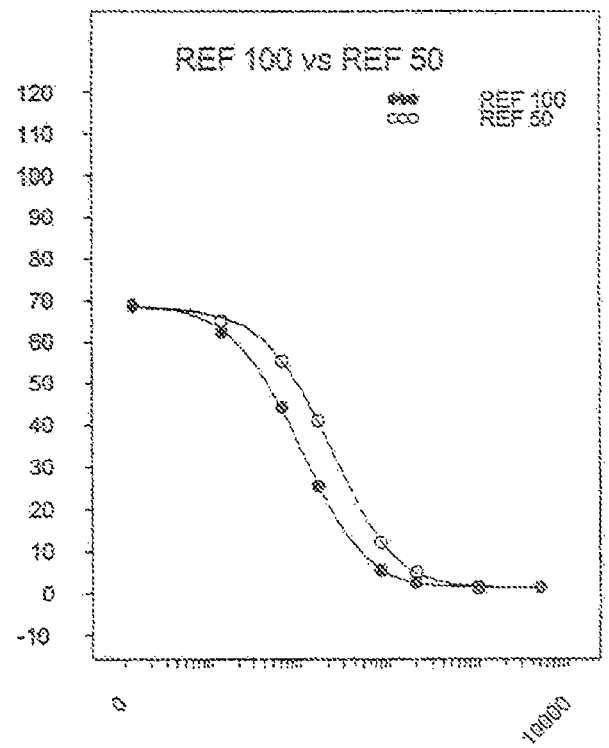
FIG. 2 is a comparison of REF100 and REF50 as described in Example 2.

Referring back to Example 1, the following exenatide solutions in acetate buffer (pH=4.5) were used as reference samples: 50% exenatide (REF50: 0.125 mg/mL); 75% exenatide (REF075: 0.188 mg/mL); 100% exenatide (REF100: 250 mg/mL); 125% exenatide (REF125: 0.313 mg/mL); and 150% exenatide (REF150: 0.375 mg/mL) The reference sample was tested against itself (thus serving as both a reference standard and a test solution) in these dilutions to show that the method quantitated the exenatide content in various exenatide-containing solutions. A comparison of REF100 and REF50 is shown in FIG. 2.

The bioassay was performed multiple times for each sample, as shown in the column with the heading "N" in Table 1 for the number of replicates for each sample. Table 1 shows that the bioassay quantitated the GLP-1 receptor activity of exenatide on 6-23 cells. All the concentrations were measured within less than 8% CV of their nominal value. This also demonstrates the ability of the bioassay to quantitate both the GLP-1 receptor activity of a GLP-1 receptor agonist compound as well as the content of the compound in a formulated vehicle.

TABLE 1

Calculated variabilities for each concentration tested (50%-150%)

| Sample | N | Mean Relative Potency | Nominal Relative Potency | SD Relative Potency | % CV1 | % CV2 |
|---|---|---|---|---|---|---|
| REF50 | 24 | 0.467 | 0.50 | 0.031 | 6.68 | 6.23 |
| REF075 | 3 | 0.758 | 0.75 | 0.053 | 7.05 | 7.13 |
| REF100 | 15 | 1.010 | 1.00 | 0.080 | 7.92 | 8.00 |
| REF125 | 3 | 1.213 | 1.25 | 0.061 | 4.99 | 4.85 |
| REF150 | 3 | 1.504 | 1.50 | 0.017 | 1.12 | 1.13 |

% CV1 = 100 * (SD/Mean Relative Potency);
% CV2 = 100 * (SD/Nominal Mean)

Example 3

Analysis of BYETTA®

This example demonstrates the utility of the bioassay to analyze pharmaceutical formulations, such as BYETTA® (e.g., 0.25 mg/mL exenatide). The bioassay was performed on three replicate BYETTA® preparations to determine the relative potency in comparison to the exenatide reference standard presented in Example 2. A control experiment was performed to demonstrate that the formulation components (e.g., mannitol, metacresol, acetate buffer) did not elicit a response in the bioassay.

BYETTA® Placebo (BPB) samples were prepared as follows: the formulation components (e.g., mannitol, metacresol, acetate buffer) were prepared at concentrations equivalent to the 1:6000 dilution of the 0.25 mg/mL BYETTA® solution. The three BPB dilutions (at 1:100, 1:10, 1:6) were prepared in the same way the exenatide test sample dilutions were prepared.

Figure 3:
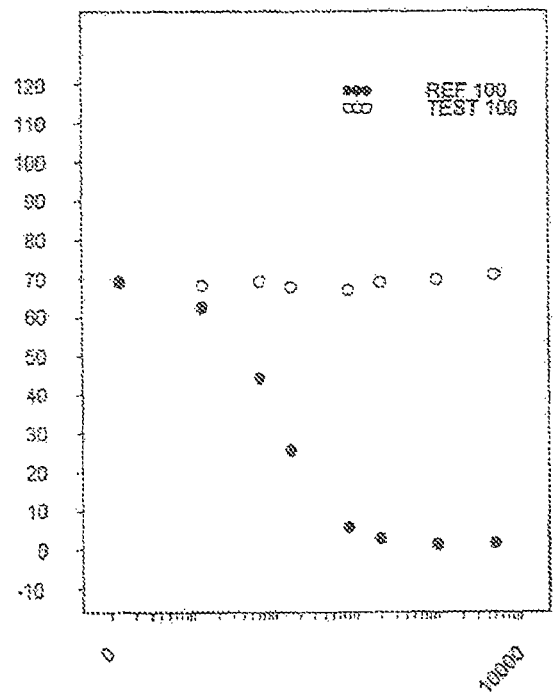
FIG. 3 is a graph comparing the REF100 to a BYETTA® Placebo (BPB) sample which only contained the BYETTA® the formulation components (e.g., mannitol, metacresol, acetate buffer) and not the active ingredient exenatide. In the figure, ○ represents BPB and ○ represents REF100. This graph demonstrates that the formulation components for BYETTA® produced no significant cAMP response compared to the exenatide reference standard.

Placebo effect: data generated from the standard (REF100) was compared to BPB response values. The DF/DFmax responses of all BPB median dilutions ranged from 66.9% to 70.9% (upper asymptote was 68.9% taken as the parameter "a" from the non-linear regression of the 5-parameter model of the reference standard) and appeared as a data scatter at values within approximately 3% of the upper asymptote of the REF100 data. As shown in FIG. 3 (where 0 represents BPB and ● represents REF100), this data demonstrates that BPB produced no significant cAMP response compared to the exenatide reference standard.

Figure 4:
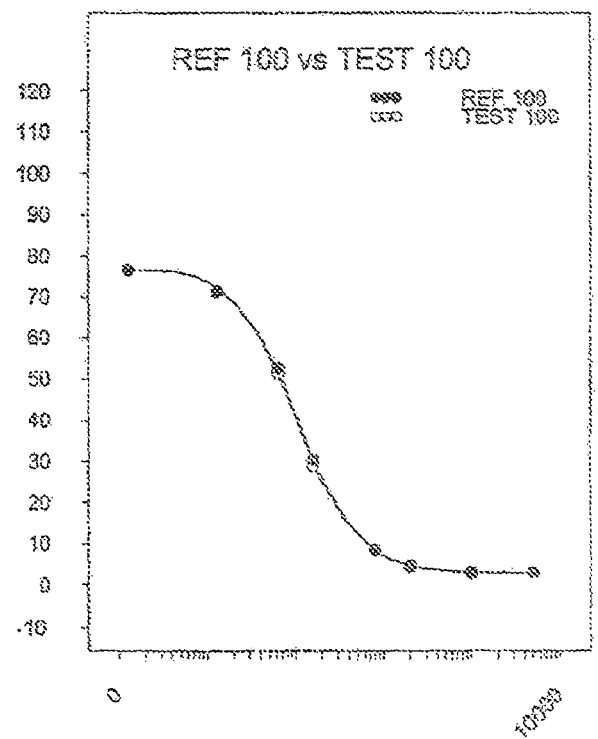
FIG. 4 is a graph comparing REF100 to BYETTA® TEST100 in Lot 1 and demonstrates that BYETTA® has a relative potency that is almost the same as that of the test standard. In the figure, ○ represents BYETTA® and ● represents REF100.

The bioassay for BYETTA® was conducted as discussed in Example 1 and the relative potencies are illustrated in Table 2. A comparison of REF100 to Lot 1 of BYETTA® TEST100 is shown in FIG. 4. BYETTA® TEST100 is the sample that corresponds to the commercial BYETTA® product (thus 100%; REF100 would be the BYETTA® reference standard, which was formulated to be the same concentration as the commercial BYETTA® product). The comparisons (not shown) of REF100 to Lots 2 and 3 of BYETTA® correspond to that of FIG. 4, as supported by Table 2. The average relative potency (N=3), standard deviation and % CV were calculated to be as follows: BYETTA® Lots 1, 2, and 3, are 105.0%, 3.0% and 2.8%, respectively.

TABLE 2

Relative Potency Results for 3 Lots of BYETTA®

| Sample | Relative Potency % |
|---|---|
| BYETTA® Lot 1 | 104.3 |
| BYETTA® Lot 2 | 108.2 |
| BYETTA® Lot 3 | 102.4 |
| Average | 105% |
| % CV | 2.8% |
| Standard Deviation | 3.0% |

Example 4

Analysis of EQW

This example demonstrates utility of this bioassay for EQW (pharmaceutical formulation of exenatide in poly(lactide-co-glycolide) microspheres; 5% theoretical exenatide load). As detailed in Example 1, experiments were performed on three EQW replicate preparations to determine the relative potency in comparison to the exenatide reference standard. Control experiments demonstrated that the formulation components (e.g., poly(lactide-co-glycolide) microspheres) did not elicit a response in the bioassay.

EQW placebo (EQWPB) (solution of 50±5 mg of bulk micro-spheres (~0% load) in 20% Acetic Acid in DMSO solution) was prepared as follows: EQWPB was in DMSO/20% AcOH containing matrix components and diluent solvents were added at a concentration equivalent to the 1:6000 dilution of the 0.25 mg/mL exenatide solution, which resulted from microsphere dissolution in DMSO/20% acetic acid. The three EQWPB dilutions were prepared in the same way as the test sample dilutions (e.g., 1:100, 1:10, 1:6).

Figure 5:
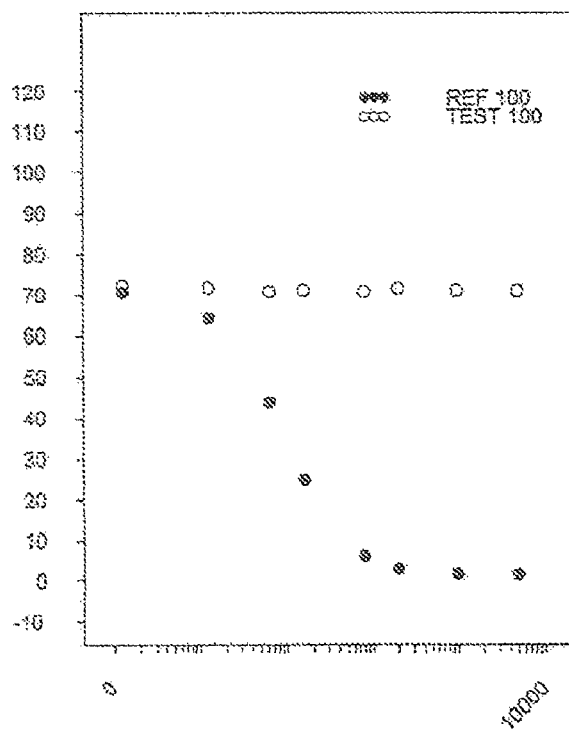
FIG. 5 is a graph comparing the REF100 to an EQW Placebo (EQWPB) sample which only contained the EQW formulation components (e.g., poly(lactide-co-glycolide) microspheres) and not the active ingredient exenatide. In the figure, ○ represents EQWPB and ● represents REF100. This graph demonstrates that the formulation components for EQW produced no significant cAMP response compared to the exenatide reference standard.
Figure 6:
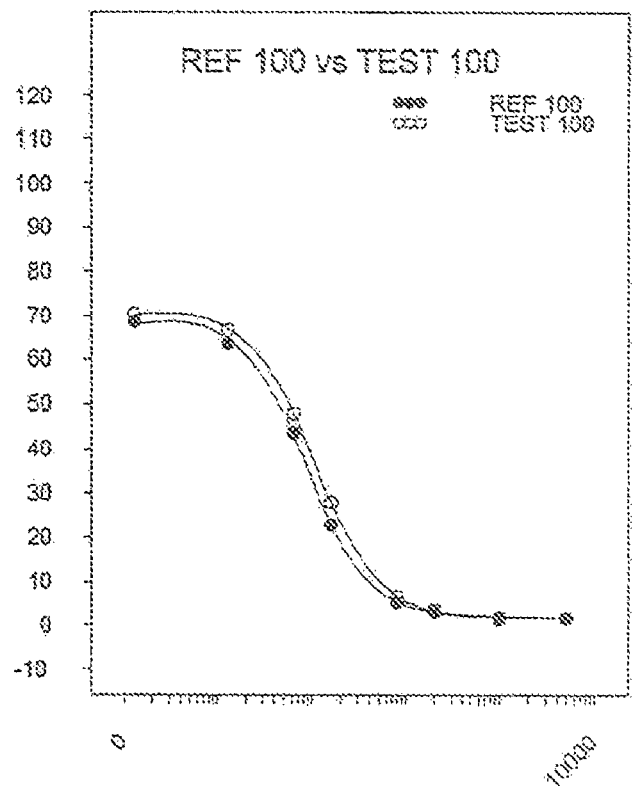
FIG. 6 is a graph comparing REF100 to EQW TEST100 in Lot 1 and demonstrates that EQW has a relative potency similar to that of the test standard. In the figure, ○ represents EQW and ● represents REF100.

Placebo response: data generated from the standard (REF100) were compared to EQWPB response values. The DF/DFmax responses of all EQWPB median dilutions ranged from 66.9% to 70.9% (upper asymptote was 68.9% taken as the parameter "a" from the non-linear regression of the 5-parameter model of the reference standard) and appeared as data scatter at values within approximately 3% of the upper asymptote of the REF100 data. As shown in FIG. 5 (where ○ represents EQWPB and o represents REF100), this data demonstrates that EQWPB produced no significant cAMP response compared to the exenatide reference standard.

The bioassay for EQW was conducted as discussed in Example 1 and the relative potencies are illustrated in Table 2. A comparison of REF100 to EQW TEST100 is shown in FIG. 5. The comparisons (not shown) of REF100 to Lots 2 and 3 of EQW correspond to that of FIG. 5, as supported by Table 3 below. The average relative potency (N=3), standard deviation and % CV were calculated to be as follows: EQW Lots 1, 2, and 3, are 80.9%, 6.8%, and 8.4%, respectively.

TABLE 3

Relative Potency Results for 3 Lots of EQW

| Sample | Relative Potency % |
| --- | --- |
| EQW Lot 1 | 78.1 |
| EQW Lot 2 | 75.9 |
| EQW Lot 3 | 88.6 |
| Average | 80.9% |
| % CV | 8.4% |
| Standard Deviation | 6.8% |

All publications cited herein are incorporated by reference in their entirety. It will be apparent to the skilled artisan that changes and modifications may be made to the detailed description without departing from the spirit or scope of the disclosure or appended claims.

What is claimed is:

1. A method for detecting or measuring glucagon-like peptide-1 (GLP-1) receptor agonist activity of a test compound comprising:
    (a) preparing a sample comprising
        (i) a test compound;
        (ii) 6-23 (clone 6) cells; and
        (iii) a detectably labeled cAMP;
    (b) forming a reaction mixture by combining the sample from step (a) and an anti cAMP antibody;
    (c) quantitatively measuring cAMP in the sample; and
    (d) correlating the amount of cAMP in the sample to the GLP-1 receptor agonist activity of the test compound.

2. The method of claim 1, wherein the sample comprises:
    (i) a pharmaceutical composition which comprises the test compound;
    (ii) 6-23 (clone 6) cells; and
    (iii) a detectably labeled cAMP.

3. The method of claim 1, further comprising incubating the reaction mixture.

4. The method of claim 1, wherein the test compound is a GLP-1 receptor agonist compound.

5. The method of claim 1, wherein the test compound is exenatide.

6. The method of claim 1, wherein the test compound is liraglutide; albiglutide; taspoglutide; LY2189265; LY2428757; lixisenatide; CJC-1134; [N$^\epsilon$-(17-carboxyheptadecanoic acid)Lys$^{20}$]exendin-4-NH$_2$; [N$^\epsilon$-(17-carboxy-heptadecanoyl)Lys$^{32}$]exendin-4-NH$_2$; [desamino-His$^1$,N$^\epsilon$-(17-carboxy-heptadecanoyl)Lys$^{20}$]exendin-4-NH$_2$; [Arg$^{12,27}$, NLe$^{14}$, N$^\epsilon$-(17-carboxyhepta-decanoyl)Lys$^{32}$]exendin-4-NH$_2$; [N$^\epsilon$-(19-carboxynonadecanoylamino)Lys$^{20}$]-exendin-4-NH$_2$; [N$^\epsilon$-(15-carboxypentadecanoylamino)Lys$^{20}$]-exendin-4-NH$_2$; [N$^\epsilon$-(13-carboxytridecanoylammo)Lys$^{20}$]exendin-4-NH$_2$; [N$^\epsilon$-(11-carboxy-undecanoylamino)Lys$^{20}$]exendin-4-NH$_2$; exendin-4-Lys$^{40}$($\epsilon$-AEEA-MPA)-NH$_2$; exendin-4-Lys$^{40}$(s-AEEA-AEEA-MPA)-NH$_2$; exendin-4-Lys$^{40}$($\epsilon$-AEEA-MPA)-NH$_2$; exendin-4-Lys$^{40}$($\epsilon$-MPA)-albumin; exendin-4-Lys$^{40}$($\epsilon$-AEEA-AEEA-MPA)-albumin; exendin-4-Lys$^{40}$($\epsilon$-AEEA-MPA)-albumin; GLP-1(7-38); desamino-His$^7$,Arg$^{26}$, Lys$^{34}$($\gamma$-Glu(N-$\alpha$-hexadecanoyl)))-GLP-1(7-37); desamino-His$^7$,Arg$^{26}$,Lys$^{34}$,(N$^\epsilon$octanoyl)-GLP-1(7-37); Arg$^{26,34}$,Lys$^{38}$(N$^\epsilon$-($\omega$carboxypentadecanoyl))-GLP-1(7-38); Arg$^{26,34}$,Lys$^{36}$(N$^\epsilon$-($\gamma$-Glu(N-$\alpha$-hexadecanoyl)))-GLP-1(7-37); or any peptide comprising the amino acid sequence of any one of SEQ ID NOs:1-40 and 43-45; wherein the peptide comprising the amino acid sequence of any one of SEQ ID NOs:25-40 may optionally be linked to the amino acid sequence of SEQ ID NO:42; wherein MPA and AEEA refer to maleimidopropionic acid and [2-(2-amino)ethoxy)lethoxy acetic acid, respectively; and wherein the test compound is optionally amidated.

7. A method for detecting or measuring GLP-1 receptor agonist activity of a test compound comprising:
    (a) preparing a sample comprising a test compound and 6-23 (clone 6) cells;
    (b) forming a reaction mixture by combining
        (i) the sample from step (a);
        (ii) an anti-cAMP antibody linked to a rare earth cryptate or a rare earth chelate; and
        (iii) cAMP linked to a fluorescent moiety;
    (c) irradiating the reaction mixture from step (b);
    (d) quantitatively determining the amount of cAMP in the sample; and
    (e) correlating the amount of cAMP in the sample to the GLP-1 receptor agonist activity of the test compound.

8. The method of claim 7, wherein the sample comprises (i) a pharmaceutical composition which comprises the test compound and (ii) 6-23 (clone 6) cells.

9. The method of claim 7, further comprising incubating the reaction mixture.

10. The method of claim 7, wherein the anti-cAMP antibody is linked to a terbium cryptate, a europium cryptate, a dysprosium cryptate, a samarium cryptate, a neodymium cryptate, a terbium chelate, a europium chelate, a dysprosium chelate, a samarium chelate, a neodymium chelate, or a combination of two or more thereof.

11. The method of claim 7, wherein the anti-cAMP antibody is an anti-cAMP monoclonal antibody.

12. The method of claim 7, wherein the fluorescent moiety is allophycocyanin, allophycocyanin B, phycocyanin C, phycocyanin R, or a combination of two or more thereof.

13. The method of claim 7, wherein the fluorescent moiety is a crosslinked allophycocyanin.

14. The method of claim 7, wherein the test compound is a GLP-1 receptor agonist compound.

15. The method of claim 7, wherein the test compound is exenatide.

16. The method of claim 7, wherein the test compound is liraglutide; albiglutide; taspoglutide; LY2189265; LY2428757; lixisenatide; CJC-1134; [N$^\epsilon$-(17-carboxyheptadecanoic acid)Lys$^{20}$]exendin-4-NH$_2$; [N$^\epsilon$-(17-carboxy-heptadecanoyl)Lys$^{32}$]exendin-4-NH$_2$; [desamino-His$^1$,N$^\epsilon$-(17-carboxy-heptadecanoyl)Lys$^{20}$]exendin-4-NH$_2$; [Arg$^{12,27}$, NLe$^{14}$,N$^\epsilon$-(17-carboxyhepta-decanoyl)Lys$^{32}$]exendin-4-NH$_2$; [N$^\epsilon$-(19-carboxynonadecanoylamino)Lys$^{20}$]-exendin-4-NH$_2$; [N$^\epsilon$-(15-carboxypentadecanoylamino)Lys$^{20}$]-exendin-4-NH$_2$; [N$^\epsilon$-(13-carboxytridecanoylammo)Lys$^{20}$]exendin-4-NH$_2$; [N$^\epsilon$-(11-carboxy-undecanoylamino)Lys$^{20}$]exendin-4-NH$_2$; exendin-4-Lys$^{40}$($\epsilon$-MPA)-NH$_2$; exendin-4-

Lys$^{40}$(s-AEEA-AEEA-MPA)-NH$_2$; exendin-4-Lys$^{40}$(ε-AEEA-MPA)-NH$_2$; exendin-4-Lys$^{40}$(ε-MPA)-albumin; exendin-4-Lys$^{40}$(ε-AEEA-AEEA-MPA)-albumin; exendin-4-Lys$^{40}$(ε-AEEA-MPA)-albumin; GLP-1(7-38); desamino-His$^7$,Arg$^{26}$, Lys$^{34}$(γ-Glu(N-α-hexadecanoyl)))-GLP-1(7-37); desamino-His$^7$,Arg$^{26}$,Lys$^{34}$,(N$^ε$octanoyl)-GLP-1(7-37); Arg$^{26,34}$,Lys$^{38}$(N$^ε$-(ωcarboxypentadecanoyl))-GLP-1(7-38); Arg$^{26,34}$,Lys$^{36}$(N$^ε$-(γ-Glu(N-α-hexadecanoyl)))-GLP-1(7-37); or any peptide comprising the amino acid sequence of any one of SEQ ID NOs:1-40 and 43-45; wherein the peptide comprising the amino acid sequence of any one of SEQ ID NOs:25-40 may optionally be linked to the amino acid sequence of SEQ ID NO:42; wherein MPA and AEEA refer to maleimidopropionic acid and [2-(2-amino)ethoxy)lethoxy acetic acid, respectively; and wherein the test compound is optionally amidated.

17. A method for detecting or measuring GLP-1 receptor agonist activity of a GLP-1 receptor agonist compound comprising the steps of:
(a) preparing a sample comprising a GLP-1 receptor agonist compound; 6-23 (clone 6) cells; and cAMP linked to a fluorescent moiety capable of emitting fluorescence at a correcting wavelength of about 665 nm;
(b) adding an agent to stimulate the sample from step (a) to produce cAMP in the 6-23 (clone 6) cells;
(c) forming a reaction mixture by combining
   (i) the sample from step (b); and
   (ii) an anti-cAMP monoclonal antibody linked to Europium-cryptate capable of generating emitted fluorescence at a measuring wavelength of about 620 nm; wherein the reaction mixture comprises a buffer capable of lysing the 6-23 (clone 6) cells;
(d) irradiating the reaction mixture from step (c) at a single excitation wavelength of about 337 nm by an external radiation source;
(e) simultaneously measuring both the emitted fluorescence at about 620 nm and the emitted fluorescence at about 665 nm which takes account interference parameters of the reaction mixture;
(f) calculating a corrected fluorescence for the fluorescence emitted by the compound at about 620 nm based on the fluorescence emitted by the compound at about 665 tun;
(g) correlating the corrected fluorescence reading to the presence or quantitative amount of cAMP in the sample; and
(h) correlating the amount of cAMP in the sample to the GLP-1 receptor agonist activity of the GLP-1 receptor agonist compound.

18. The method of claim 17, wherein the sample comprises:
(i) a pharmaceutical composition which comprises the GLP-1 receptor agonist compound, wherein the GLP-1 receptor agonist compound is exenatide;
(ii) 6-23 (clone 6) cells; and
(iii) cAMP linked to a fluorescent moiety capable of emitting fluorescence at a correcting wavelength of about 665 nm.

19. The method of claim 17, further comprising incubating the reaction mixture.

20. The method of claim 17, wherein the GLP-1 receptor agonist compound is exenatide.

* * * * *

SEQUENCE LISTING

```
<160> NUMBER OF SEQ ID NOS: 45

<210> SEQ ID NO 1
<211> LENGTH: 39
<212> TYPE: PRT
<213> ORGANISM: Heloderma suspectum
<220> FEATURE:
<221> NAME/KEY: MOD_RES
<222> LOCATION: (39)..(39)
<223> OTHER INFORMATION: AMIDATION

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Heloderma horridum
<220> FEATURE:
<221> NAME/KEY: MOD_RES
<222> LOCATION: (39)..(39)
<223> OTHER INFORMATION: AMIDATION

<400> SEQUENCE: 2

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (39)..(39)
```

<223> OTHER INFORMATION: Ser at position 39 is optionally amidated

<400> SEQUENCE: 3

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 39
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (39)..(39)
<223> OTHER INFORMATION: Ser at position 39 is optionally amidated

<400> SEQUENCE: 4

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 5
<211> LENGTH: 39
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (39)..(39)
<223> OTHER INFORMATION: Ser at position 39 is optionally amidated

<400> SEQUENCE: 5

His Gly Glu Gly Thr Phe Thr Ser Asp Leu Ser Lys Gln Leu Glu Glu
1               5                   10                  15

Glu Ala Ala Arg Leu Phe Ile Glu Phe Leu Lys Asn Gly Gly Pro Ser
            20                  25                  30

Ser Gly Ala Pro Pro Pro Ser
        35

<210> SEQ ID NO 6
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (30)..(30)
<223> OTHER INFORMATION: Gly at position 30 is optionally amidated

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

```
<210> SEQ ID NO 7
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (30)..(30)
<223> OTHER INFORMATION: Gly at position 30 is optionally amidated

<400> SEQUENCE: 7

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (30)..(30)
<223> OTHER INFORMATION: Gly at position 30 is optionally amidated

<400> SEQUENCE: 8

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (30)..(30)
<223> OTHER INFORMATION: Gly at position 30 is optionally amidated

<400> SEQUENCE: 9

His Gly Glu Gly Thr Phe Thr Ser Asp Leu Ser Lys Gln Leu Glu Glu
1               5                   10                  15

Glu Ala Ala Arg Leu Phe Ile Glu Phe Leu Lys Asn Gly Gly
            20                  25                  30

<210> SEQ ID NO 10
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (28)..(28)
<223> OTHER INFORMATION: Asn at position 28 is optionally amidated

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25
```

```
<210> SEQ ID NO 11
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)..(28)
<223> OTHER INFORMATION: Asn at position 28 is optionally amidated

<400> SEQUENCE: 11

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn
            20                  25

<210> SEQ ID NO 12
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (28)..(28)
<223> OTHER INFORMATION: Asn at position 28 is optionally amidated

<400> SEQUENCE: 12

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 13
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (28)..(28)
<223> OTHER INFORMATION: Asn at position 28 is optionally amidated

<400> SEQUENCE: 13

His Gly Glu Gly Thr Phe Thr Ser Asp Leu Ser Lys Gln Leu Glu Glu
1               5                   10                  15

Glu Ala Ala Arg Leu Phe Ile Glu Phe Leu Lys Asn
            20                  25

<210> SEQ ID NO 14
<211> LENGTH: 39
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (39)..(39)
<223> OTHER INFORMATION: Ser at position 39 is optionally amidated

<400> SEQUENCE: 14

His Gly Glu Gly Thr Phe Thr Ser Asp Leu Ser Lys Gln Leu Glu Glu
1               5                   10                  15

Lys Ala Ala Lys Glu Phe Ile Glu Phe Leu Lys Gln Gly Gly Pro Ser
            20                  25                  30

Ser Gly Ala Pro Pro Pro Ser
```

<210> SEQ ID NO 15
<211> LENGTH: 39
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (39)..(39)
<223> OTHER INFORMATION: Ser at position 39 is optionally amidated

<400> SEQUENCE: 15

His Gly Glu Gly Thr Phe Thr Ser Asp Leu Ser Lys Gln Leu Glu Glu
1               5                   10                  15

Lys Ala Ala Lys Glu Phe Ile Glu Trp Leu Lys Gln Gly Gly Pro Ser
            20                  25                  30

Ser Gly Ala Pro Pro Pro Ser
        35

<210> SEQ ID NO 16
<211> LENGTH: 39
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (14)..(14)
<223> OTHER INFORMATION: Xaa at position 14 is octyl-Gly
<220> FEATURE:
<221> NAME/KEY: MOD_RES
<222> LOCATION: (39)..(39)
<223> OTHER INFORMATION: Ser at position 39 is optionally amidated

<400> SEQUENCE: 16

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Ser
        35

<210> SEQ ID NO 17
<211> LENGTH: 39
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (34)..(34)
<223> OTHER INFORMATION: Xaa at position 34 is octyl-Gly
<220> FEATURE:
<221> NAME/KEY: MOD_RES
<222> LOCATION: (39)..(39)
<223> OTHER INFORMATION: Ser at position 39 is optionally amidated

<400> SEQUENCE: 17

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Ser Xaa Ala Pro Pro Pro Ser
        35

```
<210> SEQ ID NO 18
<211> LENGTH: 37
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (37)..(37)
<223> OTHER INFORMATION: Ser at position 37 is optionally amidated

<400> SEQUENCE: 18

His Gly Glu Phe Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser
        35

<210> SEQ ID NO 19
<211> LENGTH: 39
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (39)..(39)
<223> OTHER INFORMATION: Ser at position 39 is optionally amidated

<400> SEQUENCE: 19

His Gly Glu Phe Thr Phe Thr Ser Asp Leu Ser Lys Gln Leu Glu Glu
1               5                   10                  15

Lys Ala Ala Lys Glu Phe Ile Glu Trp Leu Lys Gln Gly Gly Pro Ser
            20                  25                  30

Ser Gly Ala Pro Pro Pro Ser
        35

<210> SEQ ID NO 20
<211> LENGTH: 39
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (39)..(39)
<223> OTHER INFORMATION: Ser at position 39 is optionally amidated

<400> SEQUENCE: 20

His Gly Glu Gly Thr Phe Thr Ser Asp Leu Val Lys Ile Leu Glu Ala
1               5                   10                  15

Glu Ala Val Arg Lys Phe Ile Glu Phe Leu Lys Asn Gly Gly Pro Ser
            20                  25                  30

Ser Gly Ala Pro Pro Pro Ser
        35

<210> SEQ ID NO 21
<211> LENGTH: 40
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (40)..(40)
<223> OTHER INFORMATION: Lys at position 40 is optionally amidated
```

-continued

```
<400> SEQUENCE: 21

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 22
<211> LENGTH: 31
<212> TYPE: PRT
<213> ORGANISM: Homo sapiens
<220> FEATURE:
<221> NAME/KEY: MOD_RES
<222> LOCATION: (31)..(31)
<223> OTHER INFORMATION: Gly at positon 31 is optionally amidated

<400> SEQUENCE: 22

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 23
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: Arg at position 30 is optionally amidated

<400> SEQUENCE: 23

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (29)..(29)
<223> OTHER INFORMATION: Aib
<220> FEATURE:
<221> NAME/KEY: MOD_RES
<222> LOCATION: (30)..(30)
<223> OTHER INFORMATION: Arg at position 30 is optionally amidated

<400> SEQUENCE: 24

His Xaa Glu Gly Thr Phe Thr Ser Asp Val Ser Ser Tyr Leu Glu Gly
1               5                   10                  15

Gln Ala Ala Arg Glu Phe Ile Ala Phe Leu Val Arg Xaa Arg
            20                  25                  30

<210> SEQ ID NO 25
<211> LENGTH: 31
<212> TYPE: PRT
<213> ORGANISM: Artificial Sequence
```

```
<220> FEATURE:
<223> OTHER INFORMATION: Synthetic polypeptide
<220> FEATURE:
<221> NAME/KEY: VARIANT
<222> LOCATION: (2)..(2)
<223> OTHER INFORMATION: Ala, Val, or Gly
<220> FEATURE:
<221> NAME/KEY: VARIANT
<222> LOCATION: (16)..(16)
<223> OTHER INFORMATION: Gly, Lys, or Glu
<220> FEATURE:
<221> NAME/KEY: VARIANT
<222> LOCATION: (17)..(17)
<223> OTHER INFORMATION: Gln or Lys
<220> FEATURE:
<221> NAME/KEY: VARIANT
<222> LOCATION: (24)..(24)
<223> OTHER INFORMATION: Ala or Glu
<220> FEATURE:
<221> NAME/KEY: VARIANT
<222> LOCATION: (27)..(27)
<223> OTHER INFORMATION: Val or Lys
<220> FEATURE:
<221> NAME/KEY: VARIANT
<222> LOCATION: (28)..(28)
<223> OTHER INFORMATION: Lys, Asn, or Arg
<220> FEATURE:
<221> NAME/KEY: VARIANT
<222> LOCATION: (30)..(30)
<223> OTHER INFORMATION: Ala or Glu; optionally amidated when 31 is
      absent
<220> FEATURE:
<221> NAME/KEY: VARIANT
<222> LOCATION: (31)..(31)
<223> OTHER INFORMATION: Gly, His, Pro, or absent; optionally amidated

<400> SEQUENCE: 25

His Ala Glu Gly Thr Phe Thr Ser Asp Val Ser Ser Tyr Leu Glu Gly
1               5                  10                  15

Gln Ala Ala Lys Glu Phe Ile Ala Trp Leu Val Lys Gly Ala Gly
            20                  25                  30

<210> SEQ ID NO 26
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (31)..(31)
<223> OTHER INFORMATION: Gly at position 31 is optionally amidated

<400> SEQUENCE: 26

His Ala Glu Gly Thr Phe Thr Ser Asp Val Ser Ser Tyr Leu Glu Gly
1               5                  10                  15

Gln Ala Ala Lys Glu Phe Ile Ala Trp Leu Val Arg Gly Arg Gly
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (31)..(31)
<223> OTHER INFORMATION: Gly at position 31 is optionally amidated

<400> SEQUENCE: 27

His Ala Glu Gly Thr Phe Thr Ser Asp Val Ser Ser Tyr Leu Glu Gly
1               5                  10                  15
```

```
Gln Ala Ala Lys Glu Phe Ile Glu Trp Leu Val Lys Gly Arg Gly
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (31)..(31)
<223> OTHER INFORMATION: Gly at position 31 is optionally amidated

<400> SEQUENCE: 28

His Ala Glu Gly Thr Phe Thr Ser Asp Val Ser Ser Tyr Leu Glu Lys
1               5                   10                  15

Gln Ala Ala Lys Glu Phe Ile Ala Trp Leu Val Lys Gly Arg Gly
            20                  25                  30

<210> SEQ ID NO 29
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (31)..(31)
<223> OTHER INFORMATION: Gly at position 31 is optionally amidated

<400> SEQUENCE: 29

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 30
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (31)..(31)
<223> OTHER INFORMATION: Gly at position 31 is optionally amidated

<400> SEQUENCE: 30

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 31
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (31)..(31)
<223> OTHER INFORMATION: Gly at position 31 is optionally amidated

<400> SEQUENCE: 31

His Gly Glu Gly Thr Phe Thr Ser Asp Val Ser Ser Tyr Leu Glu Glu
1               5                   10                  15
```

```
Gln Ala Ala Lys Glu Phe Ile Ala Trp Leu Lys Asn Gly Gly Gly
            20                  25                  30

<210> SEQ ID NO 32
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (31)..(31)
<223> OTHER INFORMATION: Gly at position 31 is optionally amidated

<400> SEQUENCE: 32

His Val Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly Gly
            20                  25                  30

<210> SEQ ID NO 33
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (31)..(31)
<223> OTHER INFORMATION: Pro at position 31 is optionally amidated

<400> SEQUENCE: 33

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro
            20                  25                  30

<210> SEQ ID NO 34
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (31)..(31)
<223> OTHER INFORMATION: Pro at position 31 is optionally amidated

<400> SEQUENCE: 34

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro
            20                  25                  30

<210> SEQ ID NO 35
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (31)..(31)
<223> OTHER INFORMATION: Pro at position 31 is optionally amidated

<400> SEQUENCE: 35

His Gly Glu Gly Thr Phe Thr Ser Asp Val Ser Ser Tyr Leu Glu Glu
1               5                   10                  15
```

Gln Ala Ala Lys Glu Phe Ile Ala Trp Leu Lys Asn Gly Gly Pro
            20                  25                  30

<210> SEQ ID NO 36
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (31)..(31)
<223> OTHER INFORMATION: Pro at position 31 is optionally amidated

<400> SEQUENCE: 36

His Val Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly Pro
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (30)..(30)
<223> OTHER INFORMATION: Gly at position 30 is optionally amidated

<400> SEQUENCE: 37

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (30)..(30)
<223> OTHER INFORMATION: Gly at position 30 is optionally amidated

<400> SEQUENCE: 38

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (30)..(30)
<223> OTHER INFORMATION: Gly at position 30 is optionally amidated

<400> SEQUENCE: 39

His Val Glu Gly Thr Phe Thr Ser Asp Val Ser Ser Tyr Leu Glu Glu
1               5                   10                  15

```
Gln Ala Ala Lys Glu Phe Ile Ala Trp Leu Lys Asn Gly Gly
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (30)..(30)
<223> OTHER INFORMATION: Gly at position 30 is optionally amidated

<400> SEQUENCE: 40

His Gly Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly
            20                  25                  30

<210> SEQ ID NO 41
<211> LENGTH: 230
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: (16)..(16)
<223> OTHER INFORMATION: Pro or Glu
<220> FEATURE:
<221> NAME/KEY: VARIANT
<222> LOCATION: (17)..(17)
<223> OTHER INFORMATION: Phe, Val or Ala
<220> FEATURE:
<221> NAME/KEY: VARIANT
<222> LOCATION: (18)..(18)
<223> OTHER INFORMATION: Leu, Glu or Ala
<220> FEATURE:
<221> NAME/KEY: VARIANT
<222> LOCATION: (80)..(80)
<223> OTHER INFORMATION: Asn or Ala
<220> FEATURE:
<221> NAME/KEY: VARIANT
<222> LOCATION: (230)..(230)
<223> OTHER INFORMATION: Lys or absent

<400> SEQUENCE: 41

Ala Glu Ser Lys Tyr Gly Pro Pro Cys Pro Pro Cys Pro Ala Pro Pro
1               5                   10                  15

Phe Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140
```

```
Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Met His Glu Ala Leu His Asn His Tyr Thr Gln Lys Ser Leu
    210                 215                 220

Ser Leu Ser Leu Gly Lys
225                 230

<210> SEQ ID NO 42
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (6)..(10)
<223> OTHER INFORMATION: Residues at positions 6-10 may be absent
<220> FEATURE:
<221> NAME/KEY: MISC_FEATURE
<222> LOCATION: (11)..(15)
<223> OTHER INFORMATION: Residues at positions 11-15 may be absent
<220> FEATURE:
<221> NAME/KEY: MISC_FEATURE
<222> LOCATION: (16)..(20)
<223> OTHER INFORMATION: Residues at positions 16-20 may be absent
<220> FEATURE:
<221> NAME/KEY: MISC_FEATURE
<222> LOCATION: (21)..(25)
<223> OTHER INFORMATION: Residues at positions 21-25 may be absent
<220> FEATURE:
<221> NAME/KEY: MISC_FEATURE
<222> LOCATION: (26)..(30)
<223> OTHER INFORMATION: Residues at positions 26-30 may be absent

<400> SEQUENCE: 42

Gly Gly Gly Gly Ser Gly Gly Gly Gly Ser Gly Gly Gly Gly Ser Gly
1               5                   10                  15

Gly Gly Ser Gly Gly Gly Gly Ser Gly Gly Gly Gly Ser
            20                  25                  30

<210> SEQ ID NO 43
<211> LENGTH: 275
<212> TYPE: PRT
<213> ORGANISM: Artificial Sequence
<220> FEATURE:
<223> OTHER INFORMATION: Synthetic polypeptide

<400> SEQUENCE: 43

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Gly Ser Gly Gly Gly Gly Ser Ala Glu
            35                  40                  45

Ser Lys Tyr Gly Pro Pro Cys Pro Pro Cys Pro Ala Pro Glu Ala Ala
        50                  55                  60

Gly Gly Pro Ser Val Phe Leu Phe Pro Pro Lys Pro Lys Asp Thr Leu
65                  70                  75                  80
```

```
Met Ile Ser Arg Thr Pro Glu Val Thr Cys Val Val Asp Val Ser
                 85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly
        275

<210> SEQ ID NO 44
<211> LENGTH: 40
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: (2)..(2)
<223> OTHER INFORMATION: Gly, D-Ala, Val, Leu, Ile, Ser or Thr
<220> FEATURE:
<221> NAME/KEY: VARIANT
<222> LOCATION: (16)..(16)
<223> OTHER INFORMATION: Gly, Glu, Asp or Lys
<220> FEATURE:
<221> NAME/KEY: VARIANT
<222> LOCATION: (27)..(27)
<223> OTHER INFORMATION: Val or Ile
<220> FEATURE:
<221> NAME/KEY: MOD_RES
<222> LOCATION: (40)..(40)
<223> OTHER INFORMATION: Cys at position 40 is optionally amidated

<400> SEQUENCE: 44

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Pro Ser
            20                  25                  30

Ser Gly Ala Pro Pro Pro Cys Cys
        35                  40

<210> SEQ ID NO 45
<211> LENGTH: 40
<212> TYPE: PRT
<213> ORGANISM: Artificial Sequence
<220> FEATURE:
```

```
-continued
<223> OTHER INFORMATION: Synthetic polypeptide
<220> FEATURE:
<221> NAME/KEY: MOD_RES
<222> LOCATION: (40)..(40)
<223> OTHER INFORMATION: Cys at position 40 is optionally amidated

<400> SEQUENCE: 45

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Gly Pro Ser
            20                  25                  30

Ser Gly Ala Pro Pro Pro Cys Cys
        35                  40
```